United States Patent [19]
Burke et al.

[11] Patent Number: 5,698,745
[45] Date of Patent: Dec. 16, 1997

[54] HYDROFORMYLATION PROCESS

[75] Inventors: Patrick Michael Burke, Wilmington, Del.; Onko Jan Gelling, Geleen, Netherlands; Henk Oevering, Stein, Netherlands; Imre Toth, Geleen, Netherlands

[73] Assignee: E. I. du Pont de Nemours and Company, Wilmington, Del.

[21] Appl. No.: 781,437

[22] Filed: Jan. 10, 1997

Related U.S. Application Data

[63] Continuation of Ser. No. 519,836, Aug. 25, 1995, abandoned.

[51] Int. Cl.$^6$ .................................................. C07C 45/50
[52] U.S. Cl. .................................. 568/454; 502/153
[58] Field of Search .................... 568/454; 502/153

[56] References Cited

U.S. PATENT DOCUMENTS

| | | | |
|---|---|---|---|
| 4,528,278 | 7/1985 | Hsu | 568/454 |
| 4,575,564 | 3/1986 | Hsu | 568/454 |

FOREIGN PATENT DOCUMENTS

| | | |
|---|---|---|
| 0 220 767 A1 | 5/1987 | European Pat. Off. |
| 0 495 547 A2 | 3/1993 | European Pat. Off. |
| 0 529 698 A2 | 3/1993 | European Pat. Off. |

OTHER PUBLICATIONS

Botteghi et al., Hydroformylation of Olefins Catalyzed by Alkene Complexes of Platinum(0), *Journal of Organometallic Chemistry*, 417, C41–C45, 1991.

*Primary Examiner*—Joseph Conrad

[57] ABSTRACT

A hydroformylation process for the production of linear aldehydes of an olefin, with hydrogen and carbon monoxide in a solvent containing a catalyst having a platinum component, a bidentate diaryl phosphine component where the bridging group is ferrocenyl, and an acid promoter component.

5 Claims, No Drawings

HYDROFORMYLATION PROCESS

This is a continuation of application Ser. No. 08/519,836 filed Aug. 25, 1995, now abandoned.

FIELD OF THE INVENTION

This invention relates to the hydroformylation of olefins to form the corresponding linear aldehyde.

BACKGROUND OF THE INVENTION

Botteghi et al. in *Journal of Organometallic Chemistry* 417 (1991) C41–C45 in an article titled "Hydroformylation of olefins catalyzed by alkene complexes of platinum(O)" disclose hydroformylation using a bidentate phosphino compound, a platinum catalyst, and an acid promoter in an organic solvent. This article notes: " . . . , internal double bonds are rather unreactive as shown by the hydroformylation of cyclohexene . . . "

U.S. Pat. No. 4,528,278 to Hsu describes a hydroformylation catalyst comprising a platinum compound, a ferrocene derived ligand and a Group IV metal halide.

An object of the present invention is to provide a process for the hydroformylation of olefins to form linear products.

SUMMARY OF THE INVENTION

The present invention is a process for the preparation of linear aldehyde which comprises contacting an olefin, hydrogen and carbon monoxide in a solvent containing a dissolved catalyst comprising (a) a platinum compound free of anionic halide, (b) a bidentate diaryl phosphine ligand having the formula $Ar_2P-Q-Ar_2P$ where Q is a ferrocenyl group and each Ar group has 6 to 15 carbon atoms, (c) an acid promoter selected from (1) sulfonic acids having a pKa in water of less than –3, (2) tetrafluoroboric acid, (3) a fluorine substituted aryl boronic acid of the formula: [HZ] +[B(Ph)$_4$]— where Z is an oxygen containing Lewis base and Ph is a fluorine or trifluoromethyl substituted phenyl group, and (4) hexafluorophosphoric acid and where the ratio (c) to (a) is in the range 0.5/1 to 3/1, and where the ratio of (b) to (a) is in the range 1.0/1 to 1.5/1.

Preferably, the olefin contains 4 to 10 carbon atoms.

The process may effectively be carried out at a temperature in the range of 80° to 120° C. and the carbon monoxide partial pressure and hydrogen partial pressure is in the range of 200 to 2000 pounds per square inch.

The present invention is also a composition comprising solvent containing a dissolved catalyst comprising, (a) a platinum compound free of anionic halide, (b) a bidentate diaryl phosphine ligand having the formula $Ar_2P-Q-PAr_2$ where Q is a ferrocenyl group and each Ar group has 6 to 15 carbon atoms, and (c) an acid promoter selected from (1) sulfonic acids having a pKa in water of less than –3, (2) tetrafluoroboric acid, (3) a fluorine substituted aryl boronic acid and hexafluorophosphoric acid; and where the ratio (c) to (a) is in the range 0.5/1 to 3/1, and where the ratio of (b) to (a) is in the range 1.0/1 to 1.5/1.

Suitable solvents include acetonitrile, adiponitrile, methylglutaronitrile, dimethyladipate, valerolactone, methylisobutylketone, methylene chloride, sulfones, such as sulfolane, mixtures of one of the above nitriles and toluene, and homogenous mixtures of the above nitriles and water. When the process of the present invention is operated in a continuous manner, the product will be removed from the solvent and the solvent recycled, and gradually the composition of the solvent will change as more an more by-products of the reaction remain in the recycled solvent.

One of the preferred bidentate diaryl phosphine ligand having the formula $Ar_2P-Q-PAr_2$ is 1,1'bis (diphenylphosphino) ferrocene.

One of the preferred acid promoters is trifluoromethane-sulfonic acid.

DETAILED DESCRIPTION

Suitable olefins for hydroformylation into linear aldelydes include: (1) pentenoic acid esters such as 2- and 3-pentenoic acid esters where the non-pentenoic acid portion is from a hydrocarbon alcohol. The hydrocarbon alcohol may be saturated or unsaturated, aliphatic or aromatic; but usually will have from 1 to 8 carbon atoms, (2) 2 and 3-pentenenitriles, (3) 2-, and 3-pentenoic acids, and (4) hydrocarbon olefins such as 4-octene, 2-butene, and 2-hexene.

The organic solvent for use in the process should dissolve the platinum catalyst compound, the compound to be hydroformylated, the bidentate diarylphosphine ligand, the acid promoter, and the product. Stated another way, the solvent should provide a homogenous reaction mixture. Suitable solvents include acetonitrile, adiponitrile, methylglutaronitrile, dimethyladipate, caprolactone, dichloromethane, 2-butanone, propylenecarbonate, valerolactone, methylisobutylketone, methylene chloride, mixtures of one of the above nitriles and toluene, homogenous mixtures of the above nitriles and water, and sulfones, such as sulfolane. When the process of the present invention is operated in a continuous manner, the product will be removed from the solvent and the solvent recycled, and gradually the composition of the solvent will change as more an more by-products of the reaction remain in the recycled solvent.

The platinum component of the catalyst must be free of anionic halide, but may contain covalent halide, e.g., fluorinated beta-diketonate. Platinum(II) beta-diketones, platinum (II)carboxylates, and platinum complexes such as Pt(cyclooctadiene)2 may be the platinum catalyst component.

The acid promoter component of the catalyst is selected from (1) sulfonic acids having a pKa in water of less than –3, (2) tetrafluoroboric acid, (3) a fluorine substituted aryl boronic acid and hexafluorophosphoric acid. Trifluoromethanesulfonic acid is one of the preferred acid. Some acids of the formula: HB(Ar)$_4$, specifically [(3,5-(CF$_3$)$_2$C$_6$H$_3$)$_4$B]-[H(OET)$_2$)]+ are also quite effective. (This is the etherate solvate of the free acid). See: Brookhart, M.; Grant, B.; and Volpe, Jr., A. F. Organometallics, 1992, 11, 3920.

The bidentate diaryl phosphine ligand having the formula $Ar_2P-Q-PAr_2$ where Q a ferrocenyl group and each of the Ar groups contain 6 to 15 carbon atoms include such compounds as:

1,1-Bis(diphenylphosphino) ferrocene; 1,1'Bis(di-m-fluorophenylphosphino) ferrocene; 1,1'Bis(di-p-methylphenylphosphino) ferrocene; 1,1'Bis (diphenylphosphino) 3,3'-(trimethylsilyl)ferrocene; 1,1'Bis(di-p-trifluoromethylphenylphosphino) ferrocene; and, 1,1'Bis(di-3,5(bis(triflouromethyl) phenylphosphino)ferrocene.

The present invention is a process for the preparation of linear aldehyde which comprises contacting an olefin, hydrogen and carbon monoxide in a solvent containing a dissolved catalyst comprising (a) a platinum compound free of anionic halide, (b) a bidentate diaryl phosphine ligand having the formula $Ar_2P-Q-Ar_2P$ where Q is a ferrocenyl group and each Ar group has 6 to 15 carbon atoms, (c) an acid promoter selected from (1) sulfonic acids having a pKa in water of less than −3, (2) tetrafluoroboric acid, (3) a fluorine substituted aryl boronic acid and hexafluorophosphoric acid and where the ratio (c) to (a) is in the range 0.5/1 to 3/1, and where the ratio of (b) to (a) is in the range 1.0/1 to 1.5/1.

In order to be most effective the ratio acid promoter to platinum compound should be is in the range 0.5/1 to 3/1, and the ratio of bidentate diaryl phosphine ligand to platinum compound should be in the range 1.0/1 to 1.5/1. The platinum component should be in the reaction mixture to the extent of 500 to 5000 parts per million parts of the reaction mixture. The usual amount of platinum component will be about 2000 parts per million parts of reaction mixture.

The process can be operated at a temperature range of 70° to 120° C., preferably at a temperature in the range of 90°–110° C.

EXAMPLES

Example 1

Hydroformylation of Hexene-2 with Pt(AcAc)$_2$+DPPF+Trifluoromethanesulfonic Acid, also called Triflic Acid in 4/1 Toluene-acetonitrile Solvent A 25 ml glass lined shaker tube was charged with 5 ml of a solution containing 0.42 g (5 mmole) 2-hexene, 19.6 mg (0.05 mmole) platinum acetylacetonate (Pt(AcAc)$_2$), 6.0 mg (0.04 mmoles) triflic acid and 50 mg tetradecane (internal GC standard) in a solvent consisting of 4 parts by weight of toluene to 1 part by weight of acetonitrile. To this solution was added 35 mg (0.0625 mmole) of 1,1'Bis (diphenylphosphino) ferrocene (DPPF).

The shaker tube was freed from air by purging first with 100 psi nitrogen (twice) and then with 1:1 CO/H$_2$ (twice). The tube was then pressurized to 700 psi CO/H$_2$ and heated 100° C. over 20 minutes. The pressure was then adjusted with 1:1 CO/H$_2$ to 1000 psi at 100° C. The temperature was maintained at 100° C. with shaker agitation for 6 hours. The heat was shut off, and the shaker tube was allowed to cool to 25°–35° C. The excess CO/H$_2$ was vented, and the product was analyzed on a capillary GC column. The results are summarized in Table 1.

|  | Mole % | Selectivities |
|---|---|---|
| Recovered Mixed Hexenes Products | 50.6 | |
| Heptanal | 20.7 | 88.5 |
| 2-Methylhexanal | 1.7 | 7.2 |
| 2-Methylpentanal | 0.3 | 1.3 |
| Hexane | 0.7 | 2.3 |
| Linearity | 91.3% | |

The results demonstrate the very high selectivity to the linear product, from an internal olefin using the above platinum catalyst. Thus, the selectivity to the desired product, heptanal is >88% at 23% conversion to aldehydes and the linearity (100* Heptanal/(all aldehydes)) is 91.3%. Note: Selectivity to a product is defined here as: 100*(Moles Product)/Sum of (moles of all products detected by the GC analysis).

In the following examples, the products were analyzed in the same way but the results are expressed in summary form as combined conversion of the olefin and its double bond isomers ("Conv"), selectivity to linear aldehyde ("Sel"), and linearity ("Lin").

Examples 2–7

Hydroformylation of Hexene-1 and Hexene-2 with DPPF Ligand and Various Acid Promoters The experiment in Example 1 was repeated except that the acid promoter and the hexene isomer were varied and where indicated, the solvent also contained water (50 or 100 equivalents per Pt). The results are shown in Table 1.

TABLE 1

| Ex | Olefin | Acid | Water Eq/Pt | Conv | Sel to Hp-al | Lin |
|---|---|---|---|---|---|---|
| 2 | Hexene-2 | HBF$_4$ | 50 | 33.8 | 90.5 | 91.5 |
| 3 | Hexene-2 | Triflic | 50 | 29.0 | 85.1 | 86.6 |
| 4 | Hexene-2 | HPF$_6$ | 50 | 28.6 | 88.7 | 89.8 |
| 5 | Hexene-1 | HBF$_4$ | 50 | 75.5 | 93.5 | 94.8 |
| 6 | Hexene-1 | HPF$_6$ | 50 | 67.4 | 93.4 | 94.8 |
| 7 | Hexene-1 | PFOSA (5/Pt) | 0 | 58.9 | 82.2 | 85.2 |

PFOSA = Perfluoro-octanesulfonic acid

The above results demonstrate that high yields of linear aldehyde can be obtained with different strong acid promoters and with both internal and terminal olefins.

Examples 8–10 M4P Hydroformylation

Hydroformylation of Methyl-4-Pentenoate (M4P) with Pt(AcAc)$_2$+DPPF+Acid

The experiment in Example 1 was repeated except that the Hexene-2 was replaced with an equivalent amount of methyl-4-pentenoate (M4P). The results are shown in Table 2.

TABLE 2

| Ex | Olefin | Acid | Water | Conv | Sel to M5FV | Lin |
|---|---|---|---|---|---|---|
| 8 | M4P | HBF$_4$ | 50 | 89.3 | 92.5 | 93.8 |
| 9 | M4P | Triflic | 50 | 85.9 | 89.7 | 93.1 |
| 10 | M4P | HPF$_6$ | 50 | 88.8 | 92.4 | 93.3 |

The above results demonstrate that high yields can be obtained with this catalyst system with a terminal functional olefin.

Example 11

M3P Hydroformylation with Pt(AcAc)$_2$+Triflic Acid in Acetonitrile Solvent

A 25 ml glass lined shaker tube was charged with 5 ml of an acetonitrile solution containing 3.42 g (30 mmole) methyl-3-pentenoate, 19.6 mg (0.05 mmole) Platinum acetylacetonate (Pt(AcAc)$_2$) and 50 mg tetradecane (internal GC standard). To this solution was added 28 mg (0.05 mmole) of 1,1'-Bis(diphenylphosphino) ferrocene and 6 mg (0.04 mmoles) of triflic acid. The solution was allowed to stand in a nitrogen atmosphere for 18 hours before commensing the hydroformylation.

The shaker tube was freed from air by filling first with 100 psi nitrogen (twice) and then with 1:1 CO/H$_2$ (twice). The tube was then pressurized to 700 psi CO/H$_2$ and heated 100° C. over 20 minutes. The pressure was then adjusted with 1:1 CO/H$_2$ to 1000 psi at 100° C. The temperature was maintained at 100° C. with shaker agitation for 6 hours. The heat was shut off, and the shaker tube was allowed to cool to 25°–35° C. The excess CO/H$_2$ was vented, and the product was analyzed for methyl esters and formylvalerates on a capillary GC column. The results are summarized in Table 3.

Examples 12–17

M3P Hydroformylation with Pt(AcAc)$_2$+Triflic Acid+ DPPF or Various Substituted DPPF Ligands in Acetonitrile Solvent The experiment in Example 11 was repeated, except that the ligand was varied to include 1,1'-Bis (diphenylphosphino) ferrocenes substituted on both the phenyl rings and the ferrocenyl moiety. The ratio of ligand to Pt and of triflic acid to Pt and the temperature were also varied. The results are shown in Table 3.

TABLE 3

| Ex | Ligand | Lig/ Pt | Trif/ Pt | Temp | Conv | Sel to M5FV | Lin | Aldol |
|----|--------|---------|----------|------|------|-------------|------|-------|
| 11 | DPPF | 1.00 | 0.8 | 100 | 69.1 | 81.1 | 91.9 | 7.1 |
| 12 | Ligand A | 1.0 | 0.8 | 100 | 64.4 | 65.9 | 90.7 | 19.5 |
| 13 | Ligand B | 1.0 | 0.8 | 100 | 24.8 | 64.5 | 81.2 | 2.4 |
| 14 | Ligand C | 1.0 | 0.8 | 100 | 50.2 | 75.3 | 89.2 | 7.8 |
| 15 | DPPF | 0.75 | 1.2 | 105 | 31.4 | 59.1 | 77.9 | 13.2 |
| 16 | DPPF | 1.5 | 1.0 | 115 | 53.3 | 79.3 | 92.2 | 1.5 |
| 17 | DPPF | 1.5 | 0.7 | 95 | 27.7 | 87.3 | 91.4 | 0.0 |

DPPF = 1,1'-Bis(diphenylphosphino)ferrocene
Ligand A = 1,1'-Bis(di-m-fluorophenylphosphino)ferrocene
Ligand B = 1,1'-Bis(di-p-tolylphosphino)ferrocene
Ligand C = 1,1'-Bis(diphenylphosphino)-3,3'-bis(trimethylsilyl)ferrocene These ligands have the following structural formulas:

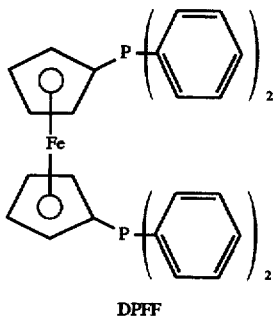

DPPF

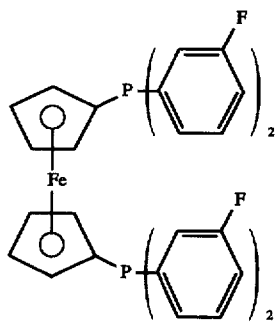

Ligand A

Ligand B

Ligand C

The results show that an internal functional olefin (M3P) can be hydroformylated with high selectivity to the linear aldehyde with an acid promoted Pt catalyst and DPPF or its substituted derivatives.

Examples 18–21

1-Hexene Hydroformylation in Sulfolane Solvent

The experiment in Example 1 was repeated except that the olefin was Hexene-1, the solvent was sulfolane and an external GC standard was used for the analysis. In some examples, water or acetonitrile was used as a co-promoter for the Pt catalyst. The results are shown in Table 4.

TABLE 4

| Ex | DPPF/ Pt | Trif/ Pt | Co-Promoter | CP/Pt | Conv | Sel to M5FV | Lin |
|----|----------|----------|-------------|-------|------|-------------|------|
| 18 | 1.25 | 0.8 | None | — | 90.3 | 86.1 | 86.6 |
| 19 | 1.25 | 0.8 | Water | 50 | 88.6 | 87.4 | 88.0 |
| 20 | 1.25 | 0.8 | CH$_3$CN | 50 | 93.1 | 91.3 | 91.8 |
| 21 | 1.25 | 0.8 | CH$_3$CN | 400 | 92.1 | 92.1 | 92.6 |

CP/Pt = Co-promoter to platinum mole ratio

The results show that high rates and selectivities can be obtained in sulfolane solvent and that rates and selectivities can be further enhanced in the presence of water or acetonitrile.

Examples 22–27

3-Pentenoic Acid Hydroformylation

The experiment in Example 1 was repeated except that the methyl-3-pentenoate was replaced with an equivalent amount of 3-pentenoic acid, the platinum source was Pt(AcAc)$_2$ and the water and acid promoter were varied. The products were analyzed directly as the formyl acids on a capillary GC column. The results are summarized in Table 5.

TABLE 5

| Ex | Acid | Acid/Pt | Ligand | Lig/Pt | H₂O/Pt | Conv | Sel to 5FVA | Lin |
|---|---|---|---|---|---|---|---|---|
| 22 | Triflic | 0.8 | DPPF | 1.25 | 50 | 83.3 | 85.1 | 91.0 |
| 23 | Triflic | 1.0 | DPPF | 1.25 | 50 | 71.4 | 65.7 | 83.2 |
| 24 | Triflic | 1.0 | DPPF | 1.25 | 0 | 66.3 | 49.5 | 72.7 |
| 25 | HBF₄ (54% aq) | 1.0 | DPPF | 1.25 | 50 | 69.1 | 81.9 | 90.7 |
| 26 | HPF₆ (60% aq) | 1.0 | DPPF | 1.25 | 50 | 80.3 | 83.8 | 90.8 |
| 27 | PFOSA | 5.0 | DPPF | 1.25 | 50 | 90.2 | 83.6 | 90.1 |

The results show that very high yield of 5-formylvaleric acid can be obtained from 3-pentenoic acid with the acid promoted platinum catalysts of this invention. Further, it can be seen that yields are improved by adding a small quantity of water (e.g., about 50 equivalents of water per equivalent of Pt).

Examples 28 3PN Hydroformylation

The experiment in Example 1 was repeated except that the M3P was replaced with 3-pentenenitrile (3PN), the mole ratio of water to Pt was 20. The products (formylvaleronitriles and valeronitrile) were analyzed directly by capillary GC. The results are summarized in Table 6.

TABLE 6

| Ex | Ligand | Lig/Pt | Conv | Sel to 5FVN* | Lin | Acctg |
|---|---|---|---|---|---|---|
| 28 | DPPF | 1.25 | 9.3 | 76.8 | 92.2 | 99 |

*5FVN=5-formylvaleronitrile

The results show that 3PN gives primarily linear product with this catalyst system.

What is claimed is:

1. A process for the preparation of linear aldehyde which comprises contacting an olefin, hydrogen and carbon monoxide in a solvent containing a dissolved catalyst comprising (a) a platinum compound free of anionic halide, (b) a bidentate diaryl phosphine ligand having the formula $Ar_2P-Q-Ar_2P$ where Q is a ferrocenyl group and each Ar group has 6 to 15 carbon atoms, (c) an acid promoter selected from (1) sulfonic acids having a pKa in water of less than −3, (2) tetrafluoroboric acid, (3) a fluorine substituted aryl boronic acid of the formula: $[HZ]+[B(Ph)_4]-$ where Z is an oxygen containing Lewis base and Ph is a fluorine or trifluoromethyl substituted phenyl group, and hexafluorophosphoric acid and where the ratio (c) to (a) is in the range 0.5/1 to 3/1, and where the ratio of (b) to (a) is in the range 1.0/1 to 1.5/1.

2. The process of claim 1 in which the olefin contains 4 to 10 carbon atoms.

3. The process of claim 1 in which the olefin is a methyl pentenoate and the linear aldehyde is methyl-5-formylvalerate.

4. The process of claim 1 in which the solvent is selected from the group consisting of acetonitrile, adiponitrile, methylglutaronitrile, dimethyladipate, valerolactone, methylisobutylketone, methylene chloride, mixtures of one of the above nitriles and toluene, and mixtures of the above nitriles and water.

5. The process of claim 1 in which the temperature is in the range of 80° to 120° C. and the carbon monoxide partial pressure is in the range of 250 to 3000 pounds per square inch.

* * * * *